United States Patent [19]

Firth

[11] 4,275,248

[45] Jun. 23, 1981

[54] PREPARATION OF 2,4,6-TRIISOPROPYLPHENOL

[75] Inventor: Bruce E. Firth, Arlington Heights, Ill.

[73] Assignee: UOP Inc., Des Plaines, Ill.

[21] Appl. No.: 138,818

[22] Filed: Apr. 9, 1980

Related U.S. Application Data

[63] Continuation-in-part of Ser. No. 51,607, Jun. 25, 1979, abandoned.

[51] Int. Cl.$^3$ .................... C07C 37/11; C07C 39/06
[52] U.S. Cl. .................................................. 568/781
[58] Field of Search ............... 568/781, 789, 790; 560/794

[56] References Cited

U.S. PATENT DOCUMENTS

| | | | |
|---|---|---|---|
| 3,367,981 | 2/1968 | Napolitano | 568/781 |
| 3,670,030 | 6/1972 | Sparks | 568/781 |
| 3,928,471 | 12/1975 | Suda et al. | 568/781 |
| 3,929,912 | 12/1975 | Hervert | 568/781 |

*Primary Examiner*—Werren B. Lone
*Attorney, Agent, or Firm*—James R. Hoatson, Jr.; Raymond H. Nelson; Eugene I. Snyder

[57] ABSTRACT

A process for introducing a plurality of alkyl groups into the aromatic ring of a hydroxy-substituted aromatic compound, whereby the available ortho sites are completely alkylated, comprises contacting said aromatic compound with olefin in the presence of a fluorided alumina as catalyst and recovering the product. The products of the process of this invention possess substantial antioxidant properties. A particular composition which shows enhanced resistance to oxidation and lowered gum formation comprises a major amount of a liquid petroleum product and from about 5 to about 500 parts per million by weight of a polyisopropyl hydroxy aromatic compound in which the available ortho positions are alkylated.

1 Claim, No Drawings

PREPARATION OF 2,4,6-TRIISOPROPYLPHENOL

CROSS-REFERENCE TO RELATED APPLICATION

This application is a continuation-in-part of my copending application, Ser. No. 51,607, filed June 25, 1979, and now abandoned, all teachings of which are hereby incorporated by reference.

BACKGROUND OF THE INVENTION

It has been known for some time that certain hydroxy aromatic compounds are effective antioxidants useful in a wide range of applications. For example, the food additive commonly known as BHA is 2-t-butyl-4-methoxyphenol. Other phenols have been utilized as antioxidants in petroleum products, in plastics, in lubricants, and in other applications where increased oxidative stability is desired. An important aspect of this invention is that certain polyalkylated hydroxy-substituted aromatics are especially effective antioxidants and, in particular, phenols in which the hydroxyl group is flanked by two alkyl groups in the ortho position show substantially greater antioxidant properties than isomeric phenols differing in the placement of the alkyl groups. Thus, to efficiently utilize this aspect of the invention, it became desirable to find a method of selectively dialkylating hydroxy-substituted aromatic compounds in the position ortho to the hydroxy group.

The methods of alkylating hydroxy-substituted aromatic componds are legion and well known to the skilled artisan in this field. Those methods based on strong acids, such as phosphoric and sulfuric acids, or strong Lewis acids, such as aluminum chloride, possess the disadvantage that considerable intramolecular rearrangement, disproportionation, and transalkylation attend the desired alkylation. Thus, the final product using such catalysts tends to reflect thermodynamic control, i.e. given sufficient time an equilibrium mixture will result. For example, monoalkylation of p-cresol with introduction of the group R using the above catalysts may give a mixture of products according to the reaction.

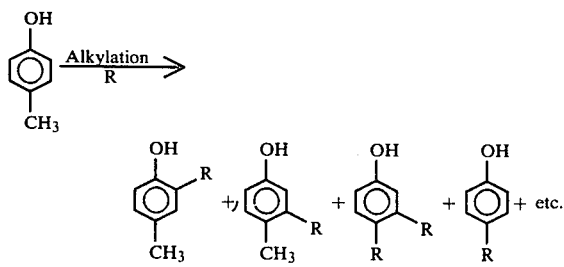

Since an object of the present invention is to provide compounds having two alkyl groups ortho to the hydroxyl, and since such compounds generally are not thermodynamically more favored than other isomeric alkylated hydroxy-substituted aromatic compounds, the kinds of catalyst described above are unsuitable for efficient synthesis of these products. An additional disadvantage of these catalysts is that the reaction product is a complex mixture of isomers and homologs so that separation of pure components is a difficult if not near-impossible task.

Use of weaker Lewis acids as catalysts alleviates the problem somewhat. Thus, in U.S. Pat. Nos. 3,290,389 and 3,367,981 are described processes in which alumina is used to alkylate phenols with preferential introduction of alkyl groups at the ortho position. However, because alumina is a relatively weak acid its catalytic activity is low relative to the stronger acids discussed above, necessitating minimum reaction temperatures of about 250° C. and above for several hours to achieve polyalkylation. At these reaction conditions several undesirable side reactions occur, such as oligomerization of the olefin used as the alkylating agent, thermal cracking of some of the reaction products, and significant disproportionation of some of the alkylated phenols thus formed. All these reactions are undesirable in the context of affording products containing relatively less of those phenols having the greatest antioxidant properties, in the context of affording complex mixtures from which separation of the most desirable components is difficult and tedious, and in the context that one of the reactants is consumed to give useless by-products.

SUMMARY OF THE INVENTION

Accordingly, a principal object of this invention is to provide a process of introducing a plurality of alkyl groups into the aromatic ring of hydroxy-substituted aromatic compounds with an olefin in the presence of a fluorided alumina catlyst and recovering the product. A more specific embodiment comprises application of the process wherein propylene is the olefin, the catalyst contains from about 0.3 to about 5 weight percent fluorine, and the reaction temperature is from about 150° to about 350° C., but preferably not over 250° C.

Other objects and embodiments will be apparent from the details provided within.

The alkylation of phenols by olefins in the presence of a catalyst is a reaction of substantial importance. Its use in the preparation of polyalkylated hydroxy-substituted aromatic compounds where the unsubstituted positions of the aromatic ring ortho to the hydroxyl group are preferentially alkylated poses a challenge. On the one hand, use of highly active catalysts tends to lead to thermodynamically controlled mixtures, where the ortho, ortho-dialkylated product is merely one of many components. On the other hand, use of less active catalysts leads to lower conversion of the reactants and permits incursion of unwanted side reactions. Another important factor is the recognition that alkylation at the ortho position is sterically hindered. In particular, after the first ortho position is alkylated, introduction of an alkyl group at the second ortho position is subject to severe steric inhibition and is disfavored kinetically as well as thermodynamically.

Alumina, especially in its gamma form, is an attractive compromise as a catalyst. For example, when phenol is treated with a 4-fold excess of propylene at 250° C. in the presence of gamma-alumina the major products are 2-isopropylphenol and 2,6-diisopropylphenol. If more strenuous conditions are employed in an attempt to obtain more di- and trialkylated products, thermal cracking and disproportionation mitigate against the utility of this catalyst. Thus, reaction of phenol with a 6-fold excess of propylene at 300° C. affords mainly 2,4,6-triisopropylphenol and some 2,6-diisopropylphenol, but fully 25% of the product is distributed among a spectrum of other polyalkylated phenols. Additionally, propylene oligomer is formed.

A discovery of this invention is that use of fluorided alumina affords desired products at temperatures of 250° C. and below, i.e. under conditions where oligomer formation and thermal cracking do not occur to any appreciable extent. Fluorided alumina is a product wherein fluoride ions have been deposited in the alumina matrix. It may be prepared, for example, by contacting alumina with a solution of ammonium fluoride, evaporating the water while mixing, and calcining the resultant product. Another mode of preparation, by way of example, is passage of gaseous hydrogen fluoride over solid alumina, wherein the contact time and the total amount of hydrogen fluoride to which the alumina is exposed will determine the final fluoride content of the product. The efficacy of the fluorided alumina catalyst in exhaustive ortho alkylation of phenols depends upon the fluorine content of the catalyst. Preparations containing from about 0.3 to about 5 weight percent fluorine are preferred, and those from about 0.3 to about 2 weight percent fluorine are particularly preferred. When fluorided alumina is used as a catalyst, reaction temperatures may be from about 150° C. to about 250° C. The desirable characteristics of this catalyst permit operation at a pressure from about 10 to about 250 atmospheres and even higher, with the reaction time being from about 1 to about 20 hours.

As an example of the efficacy of fluorided alumina, contacting phenol and an excess of propylene at an elevated temperature in the presence of a fluorided alumina gives a product containing primarily 2,6-diisopropylphenol and 2,4,6-triisopropylphenol. When a more highly fluorided alumina is used the major product shifts to 2,4,6-triisopropylphenol. Thus, by this invention the extent of alkylation can be controlled to a degree without sacrificing selectivity as to exhaustive ortho alkylation, and at a temperature where thermal cracking and disproportionation are minor considerations.

The process of this invention may be applied to a broad variety of hydroxy-substituted aromatic compounds wherein the aromatic ring may contain one or more other substituents, as aryl, alkyl, aralkyl, alkaryl, hydroxy, alkoxy, aryloxy, alkanoyloxy, amino, alkylamino, arylamino, dialkylamino, diarylamino, mercapto, alkylmercapto, and arylmercapto moieties. The process of this invention may also be applied to said aromatic compounds wherein the aromatic system is a fused-ring aromatic compound, such as naphthalene, anthracene, and the like, which also may bear one or more other substituents such as those enumerated above. Examples of suitable hydroxy substituted aromatic compounds include the cresols, ethylphenol, butylphenol, hydroquinone, hydroxyanisole, hydroxyaniline, naphthol, methyl hydroxybenzoate, methylmercaptophenol, ethylmercaptophenol, phenylmercaptophenol, hydroxydiphenyl ether, dimethylaminophenol, dibutylaminophenol, and benzylphenol.

Olefins that may be used are of the structural type $R_1CH=CHR_2$, where $R_1$ and $R_2$ are selected from the group consisting of hydrogen, an alkyl moiety having from 1 to about 20 carbon atoms, an aryl group such as phenyl, naphthyl, and substituted aryl groups. The alkyl group which becomes attached to the aromatic ring thus has no more than a disubstituted alpha carbon atom. Specific examples of olefins which may be employed include ethylene, propylene, butylene, the isomeric amylenes, isomeric hexylenes, isomeric heptylenes, isomeric octylenes, the linear internal olefins resulting from commercial dehydrogenation of n-alkanes; in the $C_{10}-C_{18}$ range, and the isomeric eicosenes.

Propylene is an especially desirable example for the group of olefins used in this invention. Among the compounds which may be made by this process are diisopropylphenol, triisopropylphenol, di- and tri-s-butylphenol, di- and tri-s-amylphenol, di- and tri-decylphenol, di- and tri-s-eicosylphenol, 2,6-di-s-butyl-4-methylphenol, 2,6-di-s-hexylmethylphenol, etc.

The process of this invention may be utilized in the batch mode. For example, a suitable reactor, such as that of the rocking autoclave type, is charged with the desired amount of hydroxy substituted aromatic compound and fluorided alumina. Thereupon, the olefin is added, and if it is desired to conduct the reaction at a pressure other than that indigenous to the various components, a suitable inert gas is admitted to the desired pressure. The reactor is sealed, mixing is commenced, and the contents are heated to the predetermined temperature. This reaction temperature is maintained for the time necessary for optimum yield of the alkylated product, generally from about 1 to about 20 hours. After the mixture is cooled, the apparatus is vented, catalyst is removed by suitable means, for example, by filtration, and product is recovered.

The process of this invention also may be practiced in a continuous mode. A reactor may contain a bed of fluorided alumina heated and maintained at the desired temperature. A mixture of hydroxy-substituted aromatic compound and the olefin may be passed through the bed at a rate such that the total contact time of reactants optimizes the product composition. Olefin and unconverted reactant may be separated from the effluent and recirculated. Product may be recovered from the effluent by suitable means, as for example by distillation.

Among the products which may be prepared by this invention, the di- and tri-isopropylated hydroxy substituted aromatic compounds are effective antioxidants for stabilizing various petroleum distillates. Examples of the latter include home heating fuel, gasoline, diesel fuel, aviaton fuel, kerosene, and lubricating oils. In this regard, 2,4,6-triisopropylphenol and 2,6-diisopropyl-4-methylphenol are particularly effective. One way of determining the stabilizing effect of additives is to compare the induction period to oxidation of a composton differing only in the nature of the additive present. When compared with a commerical product commonly used to stabilize gasoline, and which is a mixture of 2,6-di-butylphenol (75%), 2,4,6-tri-t-butylphenol (15%), and o-t-butylphenol (10%), both 2,4,6-triisopropylphenol and 2,6-diisopropyl-4-methylphenol are found to be substantially more effective in increasing the induction period, and thus are preferred additives when used as an antioxidant. The di- and tri-isopropylated phenols of the present invention may be used as antioxidants at concentrations from about 5 parts per million by weight to about 5% by weight, and preferably from about 5 to about 500 parts per million by weight when used in fuel oils.

Although all the products formed from a particular hydroxy-substituted aromatic by the process of this invention may not possess equivalent attributes, generally the most effective practice is to utilize the entire product composition without separation, partial or total, of any component. However, where it is desirable to use one particular component, or a mixture enriched in such component, separation or enrichment may be practiced by suitable means, such as by fractional distillation.

The following examples illustrate the process described in this invention. It is to be understood that said enumerated olefins and hydroxy-substituted aromatic compounds are merely representative of the class of compounds which may be used and the present invention is not necessarily limited thereto.

Examples 1-5 are reactions run in a 300 ml. rocking autoclave. The general procedure was to charge the autoclave with the desired amount of the hydroxy-substituted aromatic compound and the catalyst, following which the olefin used for alkylation was introduced. The reaction mixture was heated to the specified temperature and maintained there for the specified time. When the olefin used as propylene, pressures ranged from about 10 to about 120 atmospheres. At the end of the reaction, the mixture used was allowed to cool and, in the case of gaseous olefins, excess olefin was vented. The catalyst was separated by decantation and filtration, and the composition of the mixture was determined by gas-liquid partition chromatography (glpc).

EXAMPLE 1

A mixture of phenol (0.32 mole), propylene (1.3 mole), and 15 g. of 1% fluorided alumina was reacted at 250° C. for 4 hours. Examination by glpc showed 2,6-diisopropylphenol (30%) and 2,4,6-triisopropylphenol (60%). The diisopropyl compound was identified by comparison of its glpc retention time and nuclear magnetic resonance spectrum with those of an independently prepared authentic sample. The structure of the triisopropylphenol was inferred from its retention time and nuclear magnetic resonance spectrum.

EXAMPLE 2

Experimental conditions were similar to those of Example 1 except that 15 g. of 4.5% fluorided alumina was used. Examination by glpc showed the absence of starting material and any mono-alkylated product, the presence of about 70% 2,4,6-triisopropylphenol, and material of longer retention time.

EXAMPLE 3

In these examples, unfluorided gamma-alumina was used as the catalyst. Run 3 was performed at 250° C. with a 4-fold excess of propylene, run 4 at 300° C. with a 6-fold excess of propylene. The major products at the lower temperature were 2-isopropyl phenol (50%) and 2,6-diisopropylphenol (30%). At the higher temperature, 15% of the product was 2,6-diisopropylphenol, 60% was 2,4,6-triisopropylphenol, but the remaining 25% of product was distributed among a spectrum of polyalkylated phenols. Additionally, propylene oligomer is formed.

A comparison of the various alumina catalysts is set forth in Table 1.

TABLE 1

| ISOPROPLYATION OF PHENOL | | | | | |
|---|---|---|---|---|---|
| Run | Temp., °C. | Catalyst % F on Alumina | Molar Ratio propylene: Phenol | 2-iso-Propyl-phenol | % Yield 2,6,diiso-Propyl-phenol | 2,4,6-triiso-Propyl-phenol |
| 1 | 250 | 1 | 4 | 0 | 60 | 30 |
| 2 | 250 | 4.5 | 4 | 0 | 0 | 70 |
| 3 | 250 | 0 | 4 | 50 | 30 | |
| 4 | 300 | 0 | 6 | 0 | 15 | 60 |

The table shows the dramatic improvement in yield of the diorthoalkylated products when fluorided alumina is used, with the product being a relatively uncomplicated mixture from which the desired components may be separated with minimum difficulty. Additionally, oligomer formed when gamma-alumina was used is not formed when fluorided alumina is used as the catalyst since lower reaction temperatures are used.

EXAMPLE 4 p-Cresol (0.23 mole), propylene (0.92 mole) and 10 g. of 1% fluorided alumina were treated at 250° C. for 4 hours in a manner similar to that set forth in the above examples. Examination of the reaction mixture by glpc showed a conversion of greater than 90% of the cresol, the presence of 2,6- and 2,5-diisopropyl-4-methylphenol in a ratio of 8:1, and the absence of monoalkylated and other di- or polyalkylated products. In contrast, when gamma-alumina was used as the catalyst under identical conditions there was only a 60% conversion of p-cresol, and the product consisted of 2-isopropyl-4-methylphenol, 2,6-diisopropyl-4-methylphenol, and 2,5-diisopropyl-4-methylphenol in the ratio 75:25:1. Thus the desired ortho dialkylated product was formed in only about 15% yield with gamma-alumina, but in about 80% yield with fluorided alumina.

EXAMPLE 5

A commercial mixture of cresols, containing 65% m-cresol, 25% p-cresol, and 10% mixed xylenols and ethylphenol, was utilized as the reactant in this example. This cresol mixture (0.25 mole), propylene (0.92 mole) and 6 g. of 1% fluorided alumina were reacted at 250° C. for 4 hours. Examination by glpc showed the greater part (about 70%) of the product was the ortho dialkylated product derived from m- and p-cresol. Some monoalkylated product was inferred, as well as polyalkylated product containing more than 2 alkyl groups.

EXAMPLE 6

In this example a continuous process was employed, using a fixed bed of 1% fluorided alumina at 250° C. with a 5:1 propylene:phenol feedstock at 500 psig. at 0.5 liquid hourly space velocity. Analysis by glpc of a representative sample of reactor effluent showed the complete absence of unreacted phenol, 50% 2,4,6-triisopropylphenol, 30% 2,6-diisopropylphenol, 8% 2,4,5-triisopropylphenol, 5% 2,5-diisopropylphenol, and less than 1% propylene oligomer.

EXAMPLE 7

A continuous process was employed utilizing a fixed bed of 1% fluorided alumina with a feedstock of 4:1 propylene:p-cresol at 500 psig at 0.5 liquid hourly space velocity. Product compositions at 150°–200° C. are tabulated below.

| T. °C. | p-cresol | 2-isopropyl-4-methylphenol | 2,6-diisopropyl-4-methylphenol | 2,5-diisopropyl-4-methylphenol |
|---|---|---|---|---|
| 150 | 1 | 2 | 91 | 4 |
| 175 | — | — | 95 | 3 |
| 200 | — | — | 91 | 7 |

PRODUCT Composition, %

Thus, 2,6-diisopropyl-4-methylphenol, material which has particularly desirable antioxidant properties, is formed in yields over 90% with little if any unreacted p-cresol in a rather simple product mixture.

EXAMPLE 8

The effectiveness of materials as antioxidants in liquid petroleum products was determined by measurement of the induction period prior to oxidation, ANSI/ASTM method D525-74, and by measurement of gum formation under accelerated storage conditions, ANSI/ASTM method D873-74. The liquid petroleum product was either a base washed riser-cracked gasoline from British Petroleum Co., Canada (sample A) or a base washed, blended full range gasoline from Union Oil (sample B). Test results for various compositions are listed in Table 2. As a comparison, there is included an antioxidant of wide commercial utility which consists of 2,6-di-t-butylphenol (75%), 2,4,6-tri-t-butylphenol (15%) and 2,t-butylphenol (10%) and which we designate by the symbol E733.

TABLE 2
OXIDATIVE STABILITY OF COMPOSITIONS

| Run | Additive | Concentration (ppm) | Induction Period (minutes) A | B | Accelerated Gum (mg/100 ml) A | B |
|---|---|---|---|---|---|---|
| 1. | None | | 170 | | 45 | |
| 2. | 2,6-diisopropyl-4-methylphenol (90% purity) | 20 | 340 | | 5 | |
| | | 40 | 475 | | 3 | |
| 3. | E733 | 20 | 250 | | 6 | |
| | | 40 | 320 | | 5 | |
| 4. | None | | 125–130 | 80–105 | 180 | 320 |
| 5. | 2,6-diisopropylphenol (90% purity) | 20 | 200 | 195 | — | — |
| | | 35 | 240 | 250 | 35 | 4.5 |
| | | 50 | 305 | 310 | 9 | 3.5 |
| 6. | 2,4,6-triisopropylphenol (>85% purity) | 20 | 245 | 270 | — | 13 |
| | | 35 | 310 | 350 | 7–8 | 2.5 |
| | | 50 | 375 | 420 | 7–8 | 2.5 |
| 7. | E733 | 20 | 220 | 220 | — | — |
| | | 35 | 280 | 300 | 13 | 5 |
| | | 50 | 340 | 355 | 7 | — |

Comparison of the data shows that both 2,6-diisopropyl-4-methylphenol and 2,4,6-triisopropylphenol are substantially more effective than an accepted commercial standard in imparting oxidative stability to the gasolines tested, as measured both by a significant increase in the induction period and a significant decrease in gum formation.

I claim as my invention:

1. A process for the preparation of 2,4,6-triisopropylphenol which comprises reacting phenol with propylene at a temperature of from about 150° C. to about 250° C., at a pressure of from about 1 to about 250 atmospheres, and for a period of time from about 1 to about 20 hours in contact with a catalyst consisting essentially of fluorided alumina possessing from about 0.3 to about 5.0 wt. % fluoride to produce said 2,4,6-triisopropylphenol as the major product of said process, and recovering the resultant product.

* * * * *